United States Patent

Bister et al.

[11] Patent Number: 6,074,982
[45] Date of Patent: Jun. 13, 2000

[54] CATALYST AGENT FOR ETHERIFYING, HYDROGENATING AND ISOMERIZING CRUDE $C_4$-$C_8$- HYDROCARBON MIXTURES HAVING SULFUR CONTENT

[75] Inventors: Hans-Jürgen Bister, Düsseldorf; Arnd Stüwe, Leverkusen; Herbert Tschorn, Dormagen; Rudolf Wagner, Köln; Werner Strüver, Leverkusen, all of Germany

[73] Assignees: Bayer Aktiengesellschaft, Leverkusen; EC Erdolchemie GmbH, Cologne, both of Germany

[21] Appl. No.: 08/954,539

[22] Filed: Oct. 20, 1997

Related U.S. Application Data

[60] Continuation of application No. 08/583,409, Jan. 5, 1996, abandoned, which is a division of application No. 08/355,364, Dec. 13, 1994.

[30] Foreign Application Priority Data

Dec. 20, 1993 [DE] Germany ................................ 4343453

[51] Int. Cl.$^7$ ................................ B01J 23/00; B01J 23/40
[52] U.S. Cl. .................. 502/326; 502/325; 502/330
[58] Field of Search ..................................... 502/325, 326, 502/330

[56] References Cited

U.S. PATENT DOCUMENTS

5,008,466  4/1991  Schleppinghoff et al. ............. 568/697

*Primary Examiner*—John F. Niebling
*Assistant Examiner*—Alexander G. Ghyka
*Attorney, Agent, or Firm*—Norris, McLaughlin & Marcus, P.A.

[57] ABSTRACT

A catalytic agent for etherifying, hydrogenating and isomerizing crude $C_4$–$C_8$— hydrocarbon mixtures having a sulfur content, comprising a macroporous or gel cation exchanger having $SO_3H$ groups and being charged with a mixture of a metal selected from the group consisting of Pd, Ru, Rh and Pt with a metal selected from the group consisting of Fe, Co, Ni, Cu, Ag and W.

8 Claims, 1 Drawing Sheet

6,074,982

CATALYST AGENT FOR ETHERIFYING, HYDROGENATING AND ISOMERIZING CRUDE $C_4$-$C_8$- HYDROCARBON MIXTURES HAVING SULFUR CONTENT

This application is a continuation, of application Ser. No. 08/583,409, filed on Jan. 5, 1996, now abandoned; which is a Divisional of Ser. No. 08/355,364, filed on Dec. 13, 1994, now pending.

BACKGROUND OF THE INVENTION

1. Field of the Invention

The present invention relates to a process for the preparation of hydrocarbon mixtures having a content of alkyl tert-alkyl ethers or alkylene bis-(tert-alkyl ethers) by catalysed reaction of a crude hydrocarbon mixture with lower alkanols or alkanediols on a catalyst. Crude hydrocarbon mixtures which can be employed are those having a sulphur content of up to 1500 ppm, of which up to 500 ppm are present in the form of mercaptans, disulphides or a mixture of the two. The sulphur-resistant catalytic agent employed here is an ion exchanger having $SO_3H$ groups, which is charged with Ni, Pd or a mixture of a metal from a first group of Pd, Ru, Rh and Pt with a metal from a second group of Fe, Co, Ni, Cu, Ag and W.

The invention also relates to this catalytic agent.

In the process according to the invention, the content of highly unsaturated compounds furthermore is largely eliminated by simultaneous addition of hydrogen. Isomerization of the terminal monoolefins furthermore takes place in the process according to the invention. All these reactions effected by the catalytic agent are impaired only to a considerably reduced extent by the sulphur content of the crude hydrocarbon mixture.

2. Description of the Related Art

It has been known for a long time that light benzines and naphtha can be catalysed purely thermally or catalytically, ethylene and propylene being obtained in the desired manner; these two olefins are chiefly further processed to the corresponding polymers. In addition, such cracked products comprise further alkenes, which may be straight-chain or branched, alkanes and aromatics. For working up these products, the mixture which remains after the ethylene and propylene have been separated off are divided into distillation cuts, which in general include the range of the same carbon number or adjacent carbon numbers. The tert-alkenes present in these distillation cuts can be reacted with lower alkanols on acid catalysts to give alkyl tert-alkyl ethers. These ethers can be isolated, and are sought after solvents and octane boosters in carburettor fuels.

However, it is also possible to leave such etherified tert-alkenes in the hydrocarbon mixture and to add such a mixture to the carburettor fuel as an octane booster without further working up. In such a case, it is desirable to eliminate so-called gum-forming agents. Gum in connection with fuels is understood as meaning a content of oligomeric or polymeric substances in the fuel which occurs as an evaporation residue on analysis of the fuels. The presence of gum in fuel leads to coking and deposits in the combustion chamber of the engine and is therefore undesirable. Gum-forming agents are highly unsaturated compounds, for example diolefins and/or acetylene compounds. According to EP 197 348 B1, simultaneous etherification of the tert-alkenes and removal of the gum-forming agents by their conversion into alkenes is achieved by treating corresponding distillation cuts of such crude hydrocarbons simultaneously with methanol and hydrogen over a catalyst which comprises a commercially available cation exchanger (styrene/divinylbenzene copolymer having sulphonic acid groups) in the $H^+$ form which has been charged with palladium.

It has furthermore been found (EP 338 309 A), that it is possible additionally to carry out partial isomerization of alkenes over the ion exchanger/Pd catalysts described. Thus, for example, in the particular distillation cuts, 1-butene is rearranged into 2-butene, which is desirable for alkylations; in the distillation cuts of higher carbon number, isomerization of branched olefins is observed, in particular, such that those in which the double bond is not on the branching carbon atom are converted into those which are then tert-alkenes and thus contribute to further etherification.

It has now been found that the hydrogenation activity for elimination of the gum-forming agents, but in particular the desirable isomerization activity, of catalysts of the cation exchanger/platinum metal type, in particular those of the cation exchanger/Pd type, decreases prematurely under the influence of a high sulphur content in the crude hydrocarbon mixture and falls to a level which can no longer be utilized industrially. To eliminate such an undesirable influence by a sulphur content on catalytic reactions, it has been necessary to date to carry out a separate pretreatment of the crude hydrocarbons over an inorganic, sulphur-resistant contact catalyst or to employ another sulphur-resistant catalyst for the catalytic reaction, which, however, can no longer have the effect of the desired multiple functions like the cation exchanger/platinum metal type. Another possibility is to treat the sulphur-containing feed with a "scavenger", for example a resin carrying basic groups (anion exchanger), beforehand. This possibility entails in costs, like all additional treatments, but is only suitable for sufficiently acid S compounds: for example, mercaptan compounds are bonded, but thioether or disulphides are not.

It was therefore desirable to discover a process and suitable catalytic agents for this, which are sulphur-resistant and nevertheless can have the effect of the multiple functions described, whereby a cumbersome and cost-intensive separate removal of sulphur should be eliminated at the same time.

SUMMARY OF THE INVENTION

It has been found that such a treatment of sulphur-containing crude hydrocarbon mixtures is possible if catalytic agents based on a cation exchanger having $SO_3H$ groups which comprises the metals described below in the stated amounts are employed.

The invention therefore relates to a process for the preparation of a mixture of alkanes and alkenes having 4–8 C atoms and $C_1$–$C_8$-alkyl-tert-$C_4$–$C_8$-alkyl ethers or $C_2$–$C_8$-alkylene bis($C_4$–$C_8$-tert-alkyl ethers) which is largely free from highly unsaturated compounds and which can comprise excess $C_1$–$C_8$-alkanol or $C_2$–$C_8$-alkanediol by reaction of a) a crude hydrocarbon mixture in the range of 4–8 C atoms, which comprises $C_4$–$C_8$-tert-alkenes, in addition to other alkenes and alkanes, and comprises highly unsaturated compounds, with b) a $C_1$–$C_8$-alkanol or a $C_2$–$C_8$-alkanediol in an amount of 0.7–4, preferably 0.8–2.5, particularly preferably 1–2 OH equivalents, based on the molar amount of $C_4$–$C_8$-tert-alkene, and simultaneously with c) hydrogen in an amount of 80–500, preferably 100–200% of the amount required for hydrogenating conversion of the highly unsaturated compounds into alkenes over a macroporous or gel-like acid cation exchanger which comprises SO$_3$H groups, has a degree of crosslinking of 2–65% and a specific surface area of 5–750 m$^2$/g of dry cation exchanger and has been charged with metals, as the catalytic agent, the etherification of the tert-alkenes with the alkanols, the conversion of the highly unsaturated compounds and partial isomerization of the alkenes being carried out simultaneously, which is characterized in that a crude hydrocarbon mixture having a total sulphur content of 10–1500 ppm, of which 5–500 ppm are present in the form of mercaptans, disulphides or a mixture of the two, is employed and the cation exchanger has a content of 0.2–20 g/l of the cation exchanger, calculated as metal, of Ni, Pd or a mixture of a metal from a first group of Pd, Ru, Rh and Pt with a metal from a second group of Fe, Co, Ni, Cu, Ag and W, and in the case of a mixture, the metals of the first and second group are in a weight ratio of 1:4–4:1, preferably 1:2–2:1, relative to one another.

BRIEF DESCRIPTION OF THE DRAWING

The accompanying

DETAILED DESCRIPTION OF THE INVENTION

Figure 1:
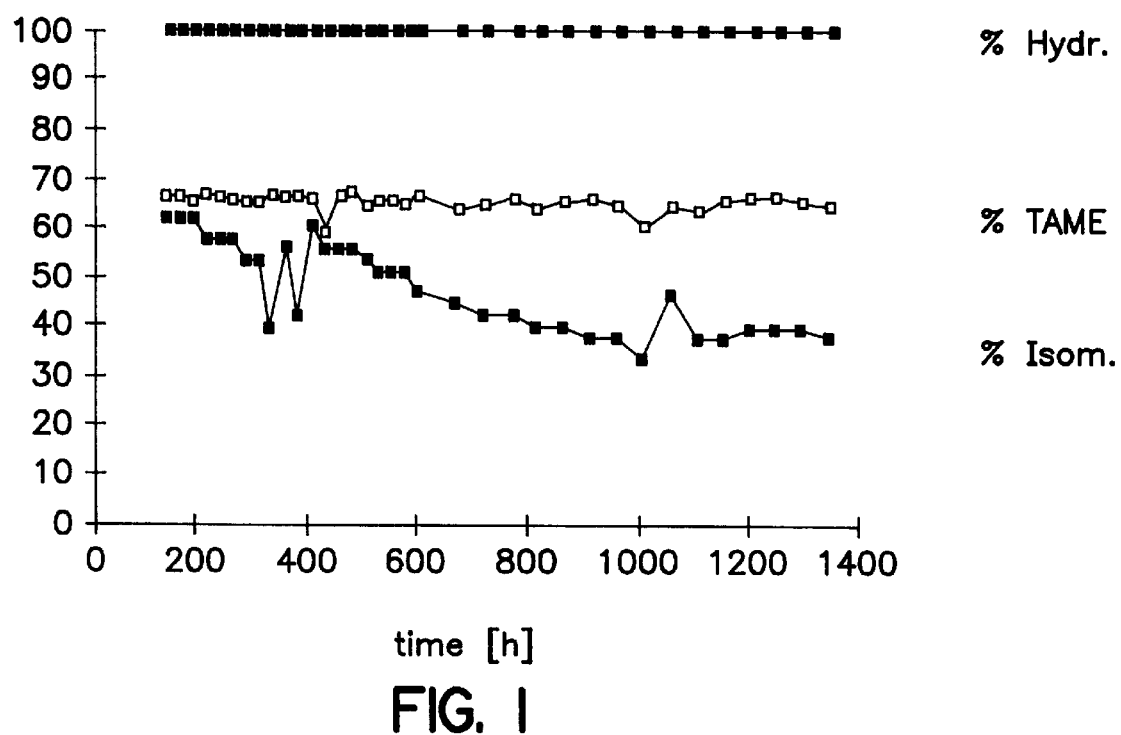
FIG. 1 shows the conversion of methyl-butenes into tert-amyl methyl ether (TAME), the hydrogenation of dienes and the isomerisation of non-tertiary methyl-butene and is discussed in more detail within Examples 5–12, process 3.

The invention furthermore relates to the catalytic agent for carrying out the above process, comprising a macroporous or gel-like cation exchanger having SO$_3$H groups, a degree of crosslinking of 2–65% and a specific surface area of 5–750 m$^2$/g of dry cation exchanger, which has with 0.2–20 g/l of cation exchanger, calculated as metal, of Ni, Pd or a mixture of a metal from a first group of Pd, Ru, Rh and Pt with a metal from a second group of Fe, Co, Ni, Cu, Ag and W, and, in the case of a mixture, the metals of the first and second group are in a weight ratio of 1:4–4:1, preferably 1:2–2:1, relative to one another.

The crude hydrocarbons to be employed according to the invention comprise tert-olefins which are accessible to etherification, such as i-butene, 2-methyl-1-butene, 2-methyl-1-pentene and others within the range of 4–8 C atoms, preferably in the range of 4–6 C atoms. The crude hydrocarbon mixtures to be employed furthermore comprise branched alkenes in which the double bond is not on the branching carbon atom but which are accessible to isomerization to give the corresponding tert-alkene, for example 3-methyl-1-butene and corresponding alkenes in the range of 5–8, preferably 5–6 C atoms.

The crude hydrocarbon mixtures to be employed furthermore comprise straight-chain and/or branched and/or cyclic saturated and monounsaturated hydrocarbons having essentially 4–8, preferably 4–6 C atoms and small amounts of the adjacent homologues of all the types of hydrocarbon mentioned, for example small amounts of C$_4$-and C$_6$-hydrocarbons in a C$_5$ distillation cut.

As gum-forming agents, the crude hydrocarbon mixtures comprise diolefins and/or acetylene compounds which lie within the boiling range of the corresponding distillation cuts and chiefly also lie in the range of the corresponding numbers of C atoms.

Such hydrocarbon mixtures having various C numbers and a different degree of unsaturation and the content of tert-olefins are available in petrochemical plants or refineries and can be obtained, for example, by reaction of naphtha, liquid petroleum gas (LPG), crude oil distillates, gas oil, natural gas condensates or other starting hydrocarbon mixtures in steam crackers, catalytic crackers (FCC) or isomerization or dehydrogenation plants. Since many of the starting substances mentioned contain sulphur, the cracked products and the distillation cuts arising therefrom also contain such an amount of sulphur. It is 10–1500 ppm, preferably 20–1000 ppm, particularly preferably 30–500 ppm of total sulphur, of which 5–500 ppm, preferably 10–400 ppm, particularly preferably 15–200 ppm, are present in the form of mercaptans, disulphides or a mixture of the two; this type of bonding of sulphur displays particularly severe deactivation of catalysts containing noble metal. The remainder of the sulphur content up to the upper limit mentioned is often in the form of thiophenes, which deactivate catalysts containing noble metal less severely. Sulphur contents occur particularly frequently in FCC products.

The composition of a C$_5$ distillation cut from a catalytic cracker may be mentioned as follows as an example of the composition of such crude hydrocarbon mixtures to be employed according to the invention:

| Substance, % by weight (approximate) | Catalytic Cracker (FCC) |
| --- | --- |
| C$_4$/light fractions | 1–5 |
| n-/i-Pentane | 30–35 |
| n-Pentene | 25–30 |
| 3-Methyl-1-butene | 0.5–2 |
| 2-Methyl-1-butene | 7–11 |
| 2 Methyl-2-butene | 15–20 |
| Cyclopentane | 1–3 |
| Diolefins/acetylenes | 0.5–5 |
| Total S | up to 1500 ppm |
| Mercaptan S | up to 500 ppm |

Alkanols and alkanediols which may be mentioned for the process according to the invention are primary or secondary, preferably primary alkanols or diols having 1–8, preferably 1–4, particularly preferably 1–2 C atoms, such as methanol, ethanol, propanol, isopropanol, butanol, isobutanol, 1-hexandol, 1-octanol, ethylene glycol, ethylene glycol monomethyl ether, diethylene glycol, 1,2- and 1,3- propylene glycol and 1,2-, 1,3- or 1,4- butylene glycol, preferably methanol, ethanol, ethylene glycol or 1-2-propylene glycol, particularly preferably methanol. The list given as examples shows that alkanols for the process according to the invention can also be monoethers of diols, and that alkanediols can also be diethers or polyethers of lower diols. In both cases, the alkyl or alkylene chain is interrupted by ether oxygen. The alkanols are employed in an amount of 0.7–4 OH equivalents/mol of total amount of tert-olefin in the crude hydrocarbon mixture; a ratio of 0.8–2.5:1 is preferred, and a ratio of 1–2:1 is particularly preferred.

It is known that the etherification of tert-alkenes with alkanols is an equilibrium reaction which can be shifted in favour of the ether by an excess of OH equivalents, based on the molar amount of tert-alkene, and in the case of i-butene leads to a yield of ether of up to 98% of the theoretical yield, but in the case of higher tert-alkenes gives decreasing yields. The mixtures obtainable according to the invention can therefore comprise excess C$_1$–C$_8$ alkanol or C$_2$–C$_8$ alkanediol.

Hydrogen is employed in the process according to the invention in an amount which is at least equimolar to that which is necessary to form monoolefins from gum-forming agents, for example in the case of a diolefin or an acetylene compound, in an amount of 1–2 mol of $H_2$/mol of diolefin or acetylene compound. Hydrogen can be employed in the pure or industrial form. Hydrogen is obtained in petrochemical plants which is accompanied by $CH_4$ and/or $N_2$ (residual gas) can advantageously be employed economically. The amount of $H_2$ in such pure or industrial hydrogens is 70 to 100% by volume of $H_2$; in $H_2$- containing residual gases from petrochemical plants, it is often about 80–90% by volume of $H_2$. Under a low operating pressure of 0.5 to 30 bar, preferably 1 to 20 bar, $H_2$ is indeed available in a relatively large excess for reasons of easier handling, but mostly flows through the reactor unused and is collected again in a collector; this $H_2$ can be recycled.

The process according to the invention is characterized by the use of the catalytic agent according to the invention which comprises a macroporous or gel-like cation exchanger which comprises $SO_3H$ groups, has a degree of crosslinking of 2–65%, preferably 8–25%, and a specific surface area of 5–750 m$^2$/g, preferably 50–250 m$^2$/g of dry cation exchanger and is charged with 0.2–20 g/l of cation exchanger of the above metals. The charging with the metal or metals is preferably 1–20 g, particularly preferably 3–15 g/l of cation exchanger. Preferred metals and combinations are Ni, Pd, Pd/Fe and Pd/Ni. The charging amounts stated are to be understood as the amount of metal alone regardless of the bonding state.

The macroporous or gel-like acid cation exchangers on which the agents are based are known to the expert and can be prepared, for example, by copolymerization of vinyl monomers and divinyl crosslinking agents, if appropriate in the presence of solvents, or by condensation of phenol and formaldehyde. Vinyl monomers are, for example, styrene or acrylic acid esters; a divinyl crosslinking agent is, for example, divinylbenzene. Acid groups of such cation exchangers are, for example, carboxyl groups, phosphonic acid groups or sulphonic acid groups. Strongly acid styrene/divinylbenzene polymers comprising sulphonic acid groups, which are commercially available under various names, are preferably employed. Macroporous cation exchangers are preferably employed. The average pore radius of the macroporous cation exchangers can vary, for example, within the limits of 50–1200 Å, preferably 70–500 Å. Such cation exchangers can have, for example, particle sizes of 0.1–2 mm as bead polymers or particle sizes of 10–100 μm as a powder resin.

To charge the cation exchanger with the metals mentioned, simple or complex cationic salts of the metals are brought together with the cation exchanger in the $H^+$ form in a manner known per se. The amount of metal salt to be applied is calculated or determined by simple preliminary experiments, so that the desired amount, calculated as metal, is present on the cationic exchanger.

Charging with the various metals can be carried out simultaneously, successively or in alternation.

The cation exchanger doped with metal is washed neutral, dried (for example at 80–100° C. in vacuo) and then treated with hydrogen for conversion of the noble metals applied into the elemental state, for example under 2–50 bar, preferably 20–30 bar, and at a temperature of 50–140° C., preferably 80–120° C. In principle, other reducing agents, such as hydrazine or formaldehyde, can also be employed. The form in which the second metal is present after the hydrogen treatment depends on the nature of the metal and on the nature of the reduction. At least the sulphonate groups charged with the noble metal are converted back into acid $SO_3H$ groups by the hydrogen treatment. The treatment with hydrogen can also be carried out in the form of activation in the reactor, before the activated=reduced catalyst is charged with the hydrocarbon mixture.

The process according to the invention is carried out at a temperature in the range of 30–140° C., preferably 35–1100° C., particularly preferably 40–90° C. A pressure is established here at which the reaction mixture, with the exception of the undissolved $H_2$, is at least partly liquid. The relationship between the operating temperature chosen and such a pressure to be established is familiar to the expert. In the process according to the invention, an LHSV (liquid hourly space velocity) of 0.1–100, preferably 0.3–20, particularly preferably 0.5–5 l of reaction mixture (crude hydrocarbon mixed with alkanol and hydrogen) per liter of catalyst per hour is established. The catalytic agent of the cation exchanger with the two metals is present here in a fixed bed or in a fluidised bed.

Simple apparatuses which are not particularly cost-intensive are in general employed for carrying out the process according to the invention. Thus, the starting substances, that is to say the crude hydrocarbon mixture, the alkanol and $H_2$, can be fed separately or together through a preheater to the reactor with the catalytic agent. After leaving the reactor with the catalytic agent, the reaction mixture is led to a stabilization reactor and is freed there from gas, for example from excess $H_2$ or any $CH_4$ or $N_2$ present, over the top. The reaction mixture withdrawn from the stabilization reactor is thus already in the finished form. This mixture can be separated into its components, for example if the alkyl tert-alkyl ethers contained therein are desired as solvents or, for example, if the isolated ethers are to be subjected to cleavage to obtain the pure i-alkene. After the removal of the ether, the olefins too can be obtained. These olefins are distinguished by an isomerization which is favourable, for example, in the context of subsequent preparation of alkylate benzine.

The mixtures according to the invention which contain alkyl tert-alkyl ethers are distinguished by an increased octane number compared with the crude hydrocarbon mixture. A hydrocarbon mixture obtainable according to the invention from a $C_5$ cut thus comprises tert-amyl methyl ether (TAME) if the reaction has been carried out with methanol. The extent of the increase in octane number by the content of TAME depends, of course, in a manner known to the expert, on the amount of i-amylenes originally present or obtained by isomerization and then etherified. The mixtures obtained according to the invention advantageously also show a reduction in sensitivity, i.e. a reduction in the difference between the motor octane number (MON) and the research octane number (RON), and, as a result of the elimination of gum-forming agents, an improvement in the colour number. For example, at a content of etherifiable alkenes in the crude hydro-carbon mixture of, for example, 10–30% by weight, a content of alkyl tert-alkyl ethers in the process products according to the invention of about 12–42% by weight is achieved.

The sensitivity drops from about 18–20 to about 13–15, and the APHA colour number is always below 8, often below 5 and can reach values below 4.

In particular, the mixtures obtained according to the invention comprise only small amounts of gum-forming agents, which guarantees that the maximum amount for gum (as evaporation residue) of 5 mg/100 ml of fuel specified in DIN 51 607 and DIN 51 600 and in the ASTM standard for automotive gasoline is reliably adhered to and not reached.

The catalytic agents according to the invention have a long service life which is influenced only a little by the content of sulphur in the crude hydrocarbon mixture.

EXAMPLE 1

Preparation of a catalyst charred with Ni and Pd 2.5 l of a strongly acid macroporous styrene/divinylbenzene resin having $SO_3H$ groups (basic resin; Bayer catalyst K 2631) were stirred in 2 l of completely demineralized water at room temperature. 3.18 g of NiO were added to the stirred dispersion. 194 g of 65% strength nitric acid were added while stirring further. The mixture was stirred for 3 hours. The product was then washed free from acid with completely demineralized water.

The catalyst charged with Ni was dispersed in 2 l of completely demineralized water. 22.7 g of palladium nitrate solution (Pd content 11% by weight) were added in the course of 30 minutes. The mixture was stirred for 15 minutes. The catalyst was washed free from nitrate with completely demineralized water.

EXAMPLE 2

Preparation of a catalyst charred with Ag and Pd 2.5 l of a strongly acid macroporous styrene/divinylbenzene resin having $SO_3H$ groups (basic resin; Bayer catalyst K 2631) were stirred in 2 l of completely demineralized water at room temperature. 2.69 g of $Ag_2O$ were added to the stirred dispersion. 194 g of 65% strength nitric acid were added while stirring further. The mixture was stirred for 3 hours. The product was then washed free from acid with completely demineralized water.

The catalyst charged with Ag was dispersed in 2 l of completely demineralized water. 22.7 g of palladium nitrate solution (Pd content 11% by weight) were added in the course of 30 minutes. The mixture was stirred for 15 minutes. The catalyst was washed free from nitrate with completely demineralized water.

EXAMPLE 3

Preparation of a catalyst charged with Fe and Pd 2.5 l of a strongly acid macroporous styrene/divinylbenzene resin having $SO_3H$ groups (basic resin; Bayer catalyst K 2631) were stirred in 2 l of completely demineralized water at room temperature. 18.08 g of $Fe(NO_3)_3.9H_2O$ were added to the stirred dispersion. The mixture was stirred for 3 hours. The product was then washed free from acid with completely demineralized water.

The catalyst charged with Fe was dispersed in 2 l of completely demineralized water. 22.7 g of palladium nitrate solution (Pd content 11% by weight) were added in the course of 30 minutes. The mixture was stirred for 15 minutes. The catalyst was washed free from nitrate with completely demineralized water.

EXAMPLE 4

Preparation of a catalyst charged with Cu and Pd 2.5 l of a strongly acid macroporous styrene/divinylbenzene resin having $SO_3H$ groups (basic resin; Bayer catalyst K 2631) were stirred in 2 l of completely demineralized water at room temperature. 3.13 g of CuO were added to the stirred dispersion. 194 g of 65% nitric acid were added while stirring further. The mixture was stirred for 3 hours. The product was then washed free from acid with completely demineralized water.

The catalyst charged with Cu was dispersed in 2 l of completely demineralized water. 22.7 g of palladium nitrate solution (Pd content 11% by weight) were added in the course of 30 minutes. The mixture was stirred for 15 minutes. The catalyst was washed free from nitrate with completely demineralized water.

EXAMPLES 5–12

Process 1:

A catalyst prepared according to example 1–4 was employed in the manner described below in a laboratory flow-through apparatus comprising a preheater, thermostatically controlled double-jacketed reactor and separator: 100 ml of catalyst was swollen in methanol for 24 hours and introduced into the flow-through reactor having an internal diameter of 25 mm and temperature measuring points at intervals of 100 mm. Activation was carried out, after rendering the apparatus inert with nitrogen, by passing hydrogen through at a rate of 30 l/hour at 100° C., initially under normal pressure for 7 hours and then under 15 bar for 7 hours. Thereafter, the starting substance was fed in.

The $C_5$ stream from a steam cracker (so-called aromatic first runnings) having a content of 11.6% by weight of 2-methyl-2-butene, 3.6% by weight of 2-methyl-1-butene (tertiary olefins) and 1.1% by weight of 3-methyl-1-butene (non-tertiary olefin) was employed as the crude hydrocarbon mixture. In addition to $C_5$-hydrocarbons, the starting substance additionally had a content of about 21% of $C_6$-hydrocarbons. The boiling range of this starting material is between 35° C. and 70° C. and the density is between 0.67 g/ml and 0.69 g/ml. This hydrocarbon mixture was mixed with 1.3 times the stoichiometric amount of methanol (based on etherifiable olefins).

The loading of the catalyst was set with a feed of 150 ml/hour to an LHSV=1, the pressure was set to 15 bar and the temperature of the double-jacketed reactor was set at 63° C. The amount of hydrogen added was adjusted such that an amount of waste gas of 10 to 15 l/hour was maintained. After a running time of 7 hours, a sample was taken and the reaction product was analysed by gas chromatography.

The values determined for the conversion to TAME (t-amyl methyl ether) the hydrogenation of the dienes and the isomerization of 3-methyl-1-butene are summarised in Table 1.

Process 2:

The experiment was carried out as in process 1, but in addition to methanol, 1200 ppm of iso-propylmercaptan (≙500 ppm of S, based on the crude hydrocarbon mixture) was additionally admixed to the starting substance.

Process 3:

The experiment was carried out as in process 1, but the catalyst according to example 1 (1 g of Ni(II)+1 g of Pd(II)) was used and 120 ppm of iso-propylmercaptan (≙50 ppm of S, based on the hydrocarbon mixture) were admixed to the starting substance. The conversions into TAME, the hydrogenation of the dienes and the isomerization of 3-methyl-1-butene as a function of the running time is shown in FIG. 1. It can be seen that, even after almost 1400 operating hours, the hydrogenation activity for highly unsaturated constituents is 100%, that the etherification is approximately constant at about 65%, based on the t-amylene present, and the percentage isomerization in the long term is established at about 40% and remains there.

TABLE 1

| Example | Catalyst | Process | ppm of S | % of TAME | % Hydrogenation | % Isomerization |
|---|---|---|---|---|---|---|
| 5 | Basic | 1 | 0 | 65 | 100 | 44 |
| 6 | resin | 2 | 500 | 65 | 95 | 16 |

TABLE 1-continued

| Example | Catalyst | Process | ppm of S | % of TAME | % Hydrogenation | % Isomerization |
|---|---|---|---|---|---|---|
| 7 | according to example 1 | 1 | 0 | 65 | 100 | 44 |
| 8 | | 2 | 500 | 65 | 97 | 35 |
| 9 | according to example 3 | 1 | 0 | 65 | 100 | 45 |
| 10 | | 2 | 500 | 65 | 100 | 32 |
| 11 | 5 g of Pd(II) by itself | 1 | 0 | 65 | 100 | 45 |
| 12 | | 2 | 500 | 65 | 100 | 46 |

What is claimed is:

1. A catalytic agent for etherifying, hydrogenating and isomerizing reaction of crude $C_4$–$C_8$-hydrocarbon mixtures of a content of 10–1500 ppm of sulphur, comprising a macroporous or gel cation exchanger which comprises $SO_3H$ groups, has a degree of crosslinking of 2–65% and a specific surface area of 5–750 m$^2$/g of dry cation exchanger and has been charged with 0.2–20 g/l calculated as metal, of a mixture of a metal selected from a first group consisting of Pd, Ru, Rh and Pt with a metal selected from a second group consisting of Fe, Co, Ni, Cu, Ag and W the metals of the first and second groups being in a weight ratio of 1:4–4:1, relative to one another.

2. The agent of claim 1, wherein the metal of the first group is Pd.

3. The agent of claim 1, wherein the metal of the second group is Fe or Ni.

4. The agent of claim 1, wherein the metals of the first and second group are in a weight ratio of 1:2–2:1.

5. The agent of claim 1, wherein the cation exchanger is a styrene/divinyl benzene resin having sulphonic acid groups.

6. The agent of claim 1, wherein the metals are present in an amount of 1–20 g/l of cation exchanger.

7. The agent of claim 6, wherein the metals are present in an amount of 3–15 g/l of cation exchanger.

8. The agent of claim 1, wherein the Pd/Fe or Pd/Ni are present as the metal.

* * * * *